US007993546B2

(12) United States Patent
Vera et al.

(10) Patent No.: US 7,993,546 B2
(45) Date of Patent: Aug. 9, 2011

(54) METHOD AND APPARATUS FOR PRECIPITATION OF NANO-STRUCTURED CARBON SOLIDS

(75) Inventors: Rodrigo B. Vera, Leeds, AL (US); Alexander P. Rutberg, Madison, AL (US)

(73) Assignee: Plasma Waste Recycling, Inc., Huntsville, AL (US)

( * ) Notice: Subject to any disclaimer, the term of this patent is extended or adjusted under 35 U.S.C. 154(b) by 504 days.

(21) Appl. No.: 12/236,240

(22) Filed: Sep. 23, 2008

(65) Prior Publication Data

US 2010/0072404 A1 Mar. 25, 2010

(51) Int. Cl.
*C07C 1/02* (2006.01)

(52) U.S. Cl. .................. 252/373; 423/418.2; 423/437.1; 423/580.1; 423/279

(58) Field of Classification Search ............... 250/493.1; 252/373; 423/418.2, 437.1, 580.1, 279, 186.21; 219/121.48; 48/61, 127.9, 197 R
See application file for complete search history.

(56) References Cited

U.S. PATENT DOCUMENTS

| | | | | |
|---|---|---|---|---|
| 4,761,515 | A * | 8/1988 | Gondouin | 585/500 |
| 6,187,226 | B1 * | 2/2001 | Detering et al. | 252/373 |
| 6,576,210 | B2 * | 6/2003 | Surma | 423/445 R |
| 7,022,293 | B2 | 4/2006 | Hogan | |
| 7,097,675 | B2 * | 8/2006 | Detering et al. | 48/127.9 |
| 7,279,655 | B2 | 10/2007 | Blutke et al. | |
| 7,354,561 | B2 * | 4/2008 | Kong | 423/279 |
| 7,704,460 | B2 * | 4/2010 | Avnery et al. | 422/186 |
| 7,833,296 | B2 * | 11/2010 | Clark | 48/61 |
| 2003/0021746 | A1 * | 1/2003 | Fincke et al. | 423/610 |
| 2004/0208805 | A1 * | 10/2004 | Fincke et al. | 422/186.04 |
| 2004/0245086 | A1 | 12/2004 | Steynberg et al. | |
| 2005/0258149 | A1 * | 11/2005 | Glukhoy et al. | 219/121.48 |
| 2006/0112639 | A1 * | 6/2006 | Nick et al. | 48/198.1 |
| 2006/0144305 | A1 | 7/2006 | Vera | |
| 2006/0185246 | A1 | 8/2006 | Hanus et al. | |
| 2006/0243582 | A1 | 11/2006 | Hazlebeck | |
| 2007/0012231 | A1 | 1/2007 | Smith et al. | |
| 2007/0060659 | A1 | 3/2007 | Kindig et al. | |
| 2007/0186472 | A1 | 8/2007 | Rabovitser et al. | |
| 2007/0225383 | A1 | 9/2007 | Cortright et al. | |
| 2009/0118561 | A1 * | 5/2009 | Vera | 588/311 |

FOREIGN PATENT DOCUMENTS

| | | |
|---|---|---|
| GB | 2423079 | 8/2006 |
| JP | 10-245201 | 9/1998 |
| JP | 2003-147373 | 5/2003 |
| WO | 2004087840 | 10/2004 |

* cited by examiner

*Primary Examiner* — Nikita Wells
*Assistant Examiner* — Johnnie L Smith
(74) *Attorney, Agent, or Firm* — George P. Kobler; Lanier Ford Shaver & Payne, P.C.

(57) ABSTRACT

An apparatus for forming nano-structures of carbon solids includes a reactor chamber into which extends a plasma torch configured to generate a plasma plume that extends into the interior of the reactor chamber. $CO_2$ from is applied to the plasma plume where the CO2 is dissociated into carbon and oxygen. A plurality of nozzles also extends into the reactor chamber, which sprays liquid water on the plume, cooling at least a portion of the carbon causing it to form solid carbon nano-structures in a mixture of liquid water. The mixture is conveyed to a flocculation tank.

18 Claims, 1 Drawing Sheet

METHOD AND APPARATUS FOR PRECIPITATION OF NANO-STRUCTURED CARBON SOLIDS

BACKGROUND

1. Field

This invention relates to apparatuses and methods for the conversion of $CO_2$ and to recovery of carbon solids.

2. Description of the Related Art $CO_2$ is known as a greenhouse gas and is believed by many to be a contributing factor in the phenomenon known as global warming. Consequently, there have been efforts to reduce the amount of $CO_2$ released to the atmosphere. These efforts typically involve reduction of the emission of $CO_2$ gas through the use of alternative energy sources. There are also efforts to reduce atmospheric $CO_2$ gas through enhancing natural $CO_2$ sinks, such as forests, oceans and soils, and developing methods to artificially sequester $CO_2$ gas.

Artificial sequestration of $CO_2$ involves capturing $CO_2$ and then depositing it in an environment in which it will not enter the atmosphere. For example, $CO_2$ is scrubbed from gas resulting from burning of fossil fuels, typically in large scale, power plants, through separation or absorption. $CO_2$ is then injected into a storage location.

One proposed form of sequestration is direct injection of $CO_2$ into the ocean at a depth wherein the $CO_2$ forms solid clathrate hydrates which ultimately dissolve into the surrounding waters. Geological sequestration of $CO_2$ has been used for some decades, through pumping $CO_2$ into declining oil wells to bring more oil to the surface, into unminable coal fields wherein the gas is absorbed into the coal, and into saline aquifers. $CO_2$ is even pumped into caves and abandoned mines.

These methods require a great deal of energy to generate and maintain the required pressure to deliver the gas, which may negate the beneficial effects of sequestration. Also, there are several safety issues that arise from these methods. Moreover, there is some question whether some methods of sequestration considered at this time might cause detrimental environmental effect. Some methods do not yield a useful by-product and, accordingly, the cost of sequestration might outweigh the benefit.

One of the biggest problems faced with disposal of $CO_2$ is the inability to convert $CO_2$ to another useful compound due to its inherent stability and the restraints of entropy. A solution to this problem is found by dissociating the $CO_2$ into elemental carbon and oxygen.

Carbon has been recently found to exist in many different and useful forms, including certain nano-structures known as "fullerenes" which include single-walled carbon nano-tubes, and buckyballs. Hence, the inventors herein have developed a beneficial method and apparatus described below to mitigate the problem of excess $CO_2$ while creating a useful product, namely, nano-structures of carbon solids.

SUMMARY

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein.

An apparatus for forming nano-structures of carbon solids includes a reactor chamber into which extends a plasma torch configured to generate a plasma plume that extends into the interior of the reactor chamber. $CO_2$ from a $CO_2$ supply is applied to the plasma plume where the CO2 is dissociated into carbon and oxygen. A plurality of nozzles also extends into the reactor chamber, which sprays liquid water on the plume, cooling at least a portion of the carbon causing it to form solid carbon nano-structures in a mixture of liquid water. The mixture is conveyed to a flocculation tank.

A process for obtaining nano-structures of solid carbon comprises the steps of first, generating a plasma plume with $CO_2$ gas, sufficient to dissociate $CO_2$ molecules into carbon and oxygen gas; and, then, cooling the plume with liquid water such that nano-structures of carbon solids are formed in a mixture with the water.

These and other embodiments of the present invention will also become readily apparent to those skilled in the art from the following detailed description of the embodiments having reference to the attached figures, the invention not being limited to any particular embodiment(s) disclosed.

BRIEF DESCRIPTION OF THE DRAWINGS

The present invention is described with reference to the accompanying drawings. In the drawings, like reference numbers indicate identical or functionally similar elements.

DETAILED DESCRIPTION

Figure 1:
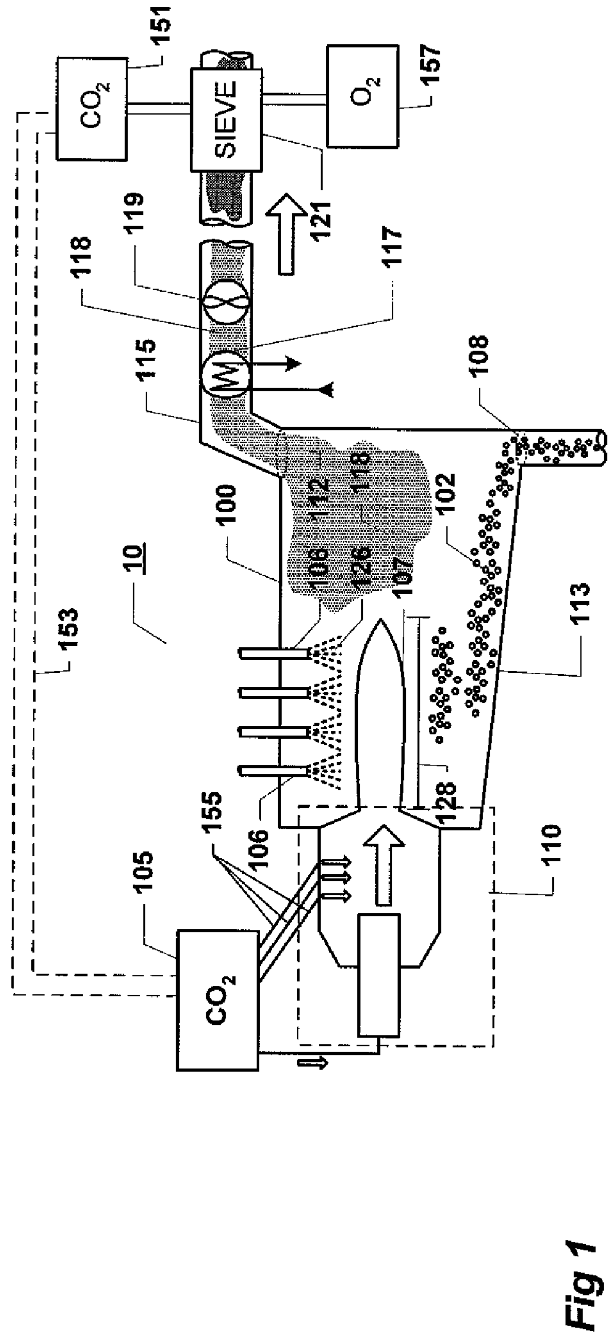
FIG. 1 is a functional diagram of an exemplary reactor section of an apparatus for obtaining nano-structures of carbon solids.
Figure 2:
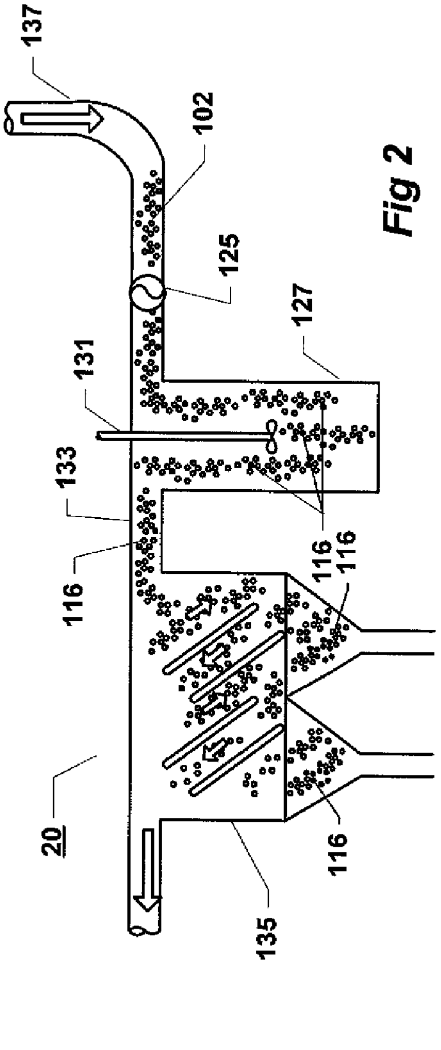
FIG. 2 is a functional diagram of an exemplary recovery section, for collecting nano-structures of carbon solids.

The various embodiments of the present invention and their advantages are best understood by referring to FIGS. 1 and 2 of the drawings. The elements of the drawings are not necessarily to scale, emphasis instead being placed upon clearly illustrating the principles of the invention. Throughout the drawings, like numerals are used for like and corresponding parts of the various drawings.

The drawings represent and illustrate examples of the various embodiments of the invention, and not a limitation thereof. It will be apparent to those skilled in the art that various modifications and variations can be made in the present inventions without departing from the scope and spirit of the invention as described herein. For instance, features illustrated or described as part of one embodiment can be included in another embodiment to yield a still further embodiment. Moreover, variations in selection of materials and/or characteristics may be practiced to satisfy particular desired user criteria. Thus, it is intended that the present invention covers such modifications as come within the scope of the features and their equivalents.

Furthermore, reference in the specification to "an embodiment," "one embodiment," "various embodiments," or any variant thereof means that a particular feature or aspect of the invention described in conjunction with the particular embodiment is included in at least one embodiment of the present invention. Thus, the appearance of the phrases "in one embodiment," "in another embodiment," or variations thereof in various places throughout the specification are not necessarily all referring to its respective embodiment.

FIG. 1 is a functional diagram of a plasma reactor apparatus 10 illustrating the inventive principles claimed hereinbelow. A reactor chamber 100 includes a plasma torch 110 suitable for generating a plasma plume 107 extending to the interior of the chamber 100. The plasma plume is generated by ionizing $CO_2$ gas from a supply 105 for the gas to enter a plasma state which is discharged in the form of a plume 107.

Once generated the plume 107 extends into the reactor chamber 100 where it is exposed to cold liquid water 126 ejected from nozzles 106 that extend into the chamber 100 through the top of the chamber 100 substantially as soon as the plume enters the chamber. The heat from the plasma torch will cause a portion of the $CO_2$ to dissociate into carbon C and oxygen O. The rapid cooling of the plasma state will cause carbon and oxygen atoms to coalesce before reforming. Some carbon will form into a variety of carbon solid structures 102 including nano-structures, for example, single-walled carbon nano-tubes, buckyballs, and other fullerenes. These carbon solids 102 are collected with unvaporized water in the bottom 113 of the chamber 100 which is sloped to induce the water/carbon solids 102 mixture to a first outlet 108.

Reactor chamber 100 is preferably a gas-tight, water-cooled vessel with an opening at one end in which the plasma torch 110 is mounted such that the plume 107 extends into the chamber 100, roughly horizontally. These gases 118 may include carbon, oxygen, CO, and unconverted $CO_2$. The chamber 100 incorporates a second outlet 112 in communication with a gas vent 115 for porting off-gases 118 from the chamber 100. Vent 115 includes a heat exchanger 117 through which the off-gas passes and is cooled, a fan 119 for creating low pressure sufficient to draw the off-gases 118 into the vent 115, and a molecular sieve 121. The off-gas 118 is then drawn away for further processing. The plasma torch 110 may be an AC or DC plasma torch or graphite arc. In an alternative configuration, $CO_2$ may be injected into the sides of the torch body through a plurality of ports 155.

Recovery of the carbon solids 102 may be achieved through a variety of methods including, without limitation, water evaporation, flocculation, and clarification. For example, referring particularly to FIG. 2, carbon solids 102 and water drained from reactor chamber 100 flow to an exemplary recovery section 20 which includes ducting 137 communicating from the first outlet 108 to a flocculation tank 127. Flocculation tank 127 may include an agitator 131 to mix flocculate with the water within the tank 127. A second section of ducting 133 is interposed between the flocculation tank 127 and a clarifier tank 135, which may be, for example, a lamella clarifier.

In operation, $CO_2$ supply 105 is a supply of concentrated $CO_2$ gas and is pressurized for delivery to the torch 110. The plasma generator imparts energy to the $CO_2$ gas to ionize it and cause it to enter a plasma state in the form of a torch plume 107. The plasma torch 110 is coupled to an end of a gas-tight reactor chamber 100 so that the plume 107 extends into the interior thereof. Although the torch 110 and plume 107 are shown at a preferable horizontal orientation, it will be understood that the orientation of the torch could be vertical or some other downward angle. It will be further understood that if the plasma torch is to be used in a vertical or angled orientation, the nozzles 106 should be adapted to extend into the reactor chamber 100 such that water spray 126 may optimally contact the plume 107. Accordingly, nozzles 106 may extend from the wall of the reactor chamber as well as from the ceiling as shown in FIG. 1. The supply of $CO_2$ must be controlled such that the temperature of the plume 107 is greater than about 1600° C. to achieve dissociation of $CO_2$.

Cold liquid water, having a temperature between about 10° C. and about 70° C., is sprayed on the plume, preferably along the entire plume length 128. The energy in the plasma causes the $CO_2$ to dissociate into its constituent elements of ionized $C^-$ and $O^+$. The exposure to the cold water rapidly quenches the plume 107 and the $C^-$ and $O^+$, causing some portion of the carbon atoms to coalesce into carbon solid structures including nano-structures such as fullerenes, nanotubes and the like. Another portion of the carbon atoms will reform with the hydrogen from the water to form various liquids of hydrocarbons ($C_xH_x$). These solids will, along with unvaporized water, will fall to the bottom 113 of the reactor chamber 100 which is sloped to allow the mixture, including carbon nano-structures 102, to flow to first outlet 108 where the mixture is conveyed to recovery section 20.

Carbon and oxygen that do not cool remain in gaseous state, forming off-gas 118 comprised of $CO_2$, CO, and $O_2$. The collection of off-gas 118 aggregates in an end of the reactor chamber 100 opposite the end where the plume 107 enters the chamber 100, and cools. The off-gas 118 is extracted through second opening 112 to vent 115 at which point the gas 118 is preferably as cool as possible, and still more preferably is less than about 70° C. The off-gas 118 is ported through a heat exchange 117 which cools the gas 118 further and drawn out by a fan 119. Optionally, the off-gas 118 then passes through molecular sieve 121 which may be configured to remove $CO_2$ 151 from the off-gas. This extracted $CO_2$ 151 may be ported back to the $CO_2$ supply 105, as shown in dashed outlined conduit 153, to be re-processed through the plasma reactor to form more carbon solids. Alternatively, a molecular sieve could be used configured to extract $O_2$ 157 from the off-gas. The remainder of the off-gas 118 may be ported away for further processing. Optionally, the off-gas may be ported back for dissociation multiple times, or may be ported to a second plasma reactor apparatus like that described above (FIG. 1, 10). The off-gas produced by reaction in this second reactor may be ported to a third reactor, and so on.

Recovery of the carbon solids 102 may be achieved through a variety of conventionally known means for separating solids from water. For example, the solids mixture 102, may be introduced into a flocculation tank 127 where the carbon solids 102 are exposed to a suitable flocculant which causes the solids 102 to floc into larger flakes, or flocculated solids 116. An agitator 131 may be used to mix flocculant with the fluid in the tank.

The mixture of water and flocculated solids 116, may then be ported to a clarifier 135, such as a lamella clarifier or other form of gravity separator, when then separates the heavier flocculated solids 116 from the water and collects them as they are allowed to fall into collection bins from which they may be retrieved.

As described above and shown in the associated drawings, the present invention comprises a method and apparatus for precipitation of nano-structured carbon solids. While particular embodiments of the invention have been described, it will be understood, however, that the invention is not limited thereto, since modifications may be made by those skilled in the art, particularly in light of the foregoing teachings. It is, therefore, contemplated by the following claims to cover any such modifications that incorporate those features or those improvements that embody the spirit and scope of the present invention.

What is claimed is:

1. A process for obtaining nano-structures of solid carbon comprising the steps of:

a. generating a plasma plume with $CO_2$ gas, said plume having a temperature greater than about 1600° C., wherein dissociation of molecules of said $CO_2$ into carbon and oxygen gas occurs; and b. cooling said plume with liquid water such that nano-structures of carbon solids are formed in a mixture with said water.

2. The process of claim 1, further comprising the steps of:

a. flocculating said carbon solids; and b. separating said flocculated carbon solids from said mixture.

3. The process of claim 1, wherein said step of generating a plasma plume results in formation of an off-gas comprised of $CO_2$, CO, and $O_2$, and further comprising the step of:

a. conveying said off-gas through a molecular sieve configured to extract at least one of $CO_2$, and $O_2$.

4. The process of claim 3, further comprising the steps of:

a. flocculating said carbon solids; and b. separating said flocculated carbon solids from said mixture.

5. The process of claim 4, further comprising the step of:

a. generating a plasma plume with said extracted $CO_2$.

6. The process of claim 1, wherein said step of generating a plasma plume results in formation of an off-gas comprised of $CO_2$, CO, and $O_2$, and further comprising the step of:

a. subjecting said off-gas to a high-energy plasma sufficient to dissociate it.

7. The process of claim 6, further comprising the steps of:

a. flocculating said carbon solids; and b. separating said flocculated carbon solids from said mixture.

8. An apparatus comprising:

a. a reactor chamber, said reactor chamber having a first outlet;

b. a plasma torch configured to generate a plasma plume that extends into the interior of said reactor chamber and wherein the temperature of said plume is greater than about 1600° C.;

c. a supply of $CO_2$ in communication with said plasma torch, such that $CO_2$ from said supply is applied to said plasma plume and said $CO_2$ is dissociated into carbon and oxygen;

d. a plurality of nozzles extending into the interior of said reactor chamber, wherein each of said plurality of nozzles is oriented to direct a spray of liquid water upon said plume, such that at least a portion of said carbon cools and forms solid carbon nano-structures in a mixture of liquid water; and e. a tank, within which is a flocculate, having an inlet in communication with said first outlet, said flocculate being suitable for flocculating said nano-structures within said mixture.

9. The apparatus of claim 8, wherein said reactor chamber includes a second outlet through which an off-gas exits said reactor chamber, said off-gas comprising at least $CO_2$, CO, and $O_2$.

10. The apparatus of claim 9, further comprising a molecular sieve in communication with said second outlet, wherein said molecular sieve is configured to extract at least one of $CO_2$ and $O_2$.

11. The apparatus of claim 10, wherein said molecular sieve is configured to extract $CO_2$ and includes a port in communication with said supply of $CO_2$.

12. The apparatus of claim 8, further comprising a separator in communication with said tank for separating said flocculated nano-structures from said mixture.

13. The apparatus of claim 12, wherein said reactor chamber includes a second outlet through which an off-gas exits said reactor chamber, said off-gas comprising at least $CO_2$, CO, and $O_2$.

14. The apparatus of claim 13, further comprising a molecular sieve in communication with said second outlet, wherein said molecular sieve is configured to extract at least one of $CO_2$ and $O_2$.

15. The apparatus of claim 14, wherein said molecular sieve is configured to extract $CO_2$ and includes a port in communication with said supply of $CO_2$.

16. An apparatus comprising:

a. a plasma torch for ejecting a plasma plume into a reactor chamber, said plasma torch configured to generate said plume with $CO_2$ at a temperature greater than about 1600° C.;

b. a sprayer for spraying liquid water into said reactor chamber onto said plume such that carbon proximal to said plume is cooled to form nano-structures of carbon solids present in a mixture with said water;

c. a flocculation tank in communication with said reactor chamber;

d. a separator in communication with said flocculation tank; and e. a molecular sieve in communication with said reactor chamber.

17. The apparatus of claim 16, wherein said molecular sieve is configured to extract at least one of $CO_2$ and $O_2$ from an off-gas comprised of at least $CO_2$, CO, and $O_2$.

18. The apparatus of claim 17, wherein said molecular sieve is configured to extract $CO_2$ and is in communication with said plasma torch.

* * * * *